United States Patent [19]

Nishihira et al.

[11] Patent Number: 5,276,200
[45] Date of Patent: Jan. 4, 1994

[54] METHOD OF PREPARING SODIUM FORMYL ACETONE AND 4,4-DIMETHOXY-2-BUTANONE

[75] Inventors: Keigo Nishihira; Shuji Tanaka; Masahiro Kondo, all of Ube, Japan

[73] Assignee: Ube Industries, Ltd., Yamagushi, Japan

[21] Appl. No.: 961,402

[22] Filed: Oct. 15, 1992

[30] Foreign Application Priority Data

Oct. 18, 1991 [JP] Japan .................................. 3-333835
Nov. 26, 1991 [JP] Japan .................................. 3-355390

[51] Int. Cl.$^5$ .............................................. C07C 45/64
[52] U.S. Cl. ...................................... 568/392; 568/391
[58] Field of Search .................................. 568/391, 392

[56] References Cited

U.S. PATENT DOCUMENTS 2,760,985  8/1956  Burness ................................. 568/392
2,760,986  8/1956  Fletcher et al. ..................... 568/391
2,760,987  8/1956  Burness ................................. 568/391

Primary Examiner—James H. Reamer
Attorney, Agent, or Firm—Merchant, Gould, Smith, Edell, Welter & Schmidt

[57] ABSTRACT

The present invention provides a method of preparing sodium formyl acetone using acetone, methyl formate and sodium methoxide as raw materials. A mixture consisting of an acetone and a methyl formate is supplied to a methanol solution of sodium methoxide, or an acetone and a methyl formate are separately supplied simultaneously to the methanol solution of sodium methoxide. The resultant mixture is sufficiently stirred over a predetermined period of time so as to carry out the reaction to form sodium formyl acetone. Also provided is a method of preparing 4,4-dimethoxy-2-butanone. In this method, the reaction mixture obtained in the reaction to form sodium formyl acetone is directly charged into a reaction vessel simultaneously with sulfuric acid to neutralize and acetalize sodium formyl acetone contained in the reaction mixture so as to obtain 4,4-dimethoxy-2-butanone.

15 Claims, No Drawings

METHOD OF PREPARING SODIUM FORMYL ACETONE AND 4, 4-DIMETHOXY-2-BUTANONE

BACKGROUND OF THE INVENTION

1. Field of the Invention

The present invention relates to a method of preparing sodium formyl acetone and 4,4-dimethoxy-2-butanone. Each of sodium formyl acetone, which has ketone and aldehyde group in the molecule, and 4,4-dimethoxy-2-butanone, which is obtained by neutralizing and acetalizing sodium formyl acetone, is useful as a raw material in the synthesis of organic materials such as medicines and agricultural chemicals.

2. Description of the Related Art

A method of preparing sodium formyl acetone using as raw materials acetone, methyl formate and sodium methoxide is described in U.S. Pat. No. 2,760,985. In this method, a powdery sodium methoxide is used as a raw material. It should be noted that a powdery sodium methoxide tends to react with oxygen and tends to be decomposed by the moisture within the air. It follows that the loss of sodium methoxide, which is costly, leads to a high preparing cost of sodium formyl acetone. What should also be noted is that sodium methoxide, if attached to the human skin, causes scalding or the like, making it troublesome to handle a powdery sodium methoxide. Further, sodium methoxide in the reacting stage is in the form of a slurry having a very high viscosity, with the result that the mixing of the slurry for achieving a sufficient reaction within a reaction vessel is made difficult in the industrial production of sodium formyl acetone.

A method of preparing 4,4-dimethoxy-2-butanone by neutralizing and acetalizing sodium formyl acetone is also disclosed in U.S. Pat. No. 2,760,985. In this method, sodium formyl acetone is isolated as a solid material and, then, dissolved again in methanol when used in the preparation of 4,4-dimethoxy-2-butanone. It should be noted that a solid sodium formyl acetone is deliquescent, making it troublesome to handle the solid sodium formyl acetone. Further, use of a solid material is low in productivity in unit operation of separation, feeding, transportation, mixing, etc., compared with use of a liquid material. Thus, it is not desirable to use a solid material in the industrial production of 4,4-dimethoxy-2-butanone. What should also be noted is that hydrochloric acid is used in this method as a neutralizing and acetalizing reagent. Naturally, it is necessary to use an apparatus formed of a material selected in view of resistance to corrosion caused by chlorine, leading to a high equipment cost.

As described above, a solid sodium methoxide is used in the conventional method of preparing sodium formyl acetone using as raw materials acetone, methyl formate and sodium methoxide. The solid phase catalytic reaction employed in the conventional method is poor in reproducibility and necessitates troublesome operations, compared with a liquid-liquid reaction. In addition, the conventional method, when employed in the industrial production of sodium formyl acetone, is not sufficiently high in yield.

The conventional method of preparing 4,4-dimethoxy-2-butanone by neutralizing and acetalizing sodium formyl acetone also leaves much room for further improvement when the method is employed for the industrial production of 4,4-dimethoxy-2-butanone. For example, the conventional method is unsatisfactory in operability and necessitates an apparatus formed of special materials.

An object of the present invention is to provide a method of industrially producing sodium formyl acetone of high purity with a high yield using acetone, methyl formate and sodium methoxide as raw materials. For improving industrial operability, a liquid-liquid reaction is employed in the method of the present invention so as to simplify the industrial producing process.

Another object is to provide a method of industrially producing 4,4-dimethoxy-2-butanone with a high yield from sodium formyl acetone. The method of the present invention permits overcoming the above-noted problems inherent in the prior art.

SUMMARY OF THE INVENTION

The present inventors have conducted an extensive study in an attempt to solve the above-noted various problems inherent in the conventional methods of preparing sodium formyl acetone and 4,4-dimethoxy-2-butanone, arriving at a method of preparing sodium formyl acetone, in which sodium methoxide is supplied to a reaction system in the form of a methanol solution so as to carry out a liquid phase reaction, and at a method of preparing 4,4-dimethoxy-2-butanone, in which a reaction mixture containing sodium formyl acetone is directly subjected to neutralization and acetalization with sulfuric acid, without isolating sodium formyl acetone from the reaction mixture, use of sulfuric acid making it possible to carry out the reaction within an apparatus formed of ordinary materials.

According to an aspect of the present invention, there is provided a method of preparing sodium formyl acetone using acetone, methyl formate and sodium methoxide as raw materials, wherein a mixture of acetone and methyl formate is supplied into a methanol solution of sodium methoxide, or an acetone and a methyl formate are separately supplied simulataneously into a methanol solution of sodium methoxide, and the raw materials are mixed, over a predetermined period of time such that acetone is not excessively present in the reaction system so as to react acetone with methyl formate and sodium methoxide.

According to another aspect of the present invention, there is provided a method of preparing 4,4-dimethoxy-2-butanone, wherein the reaction mixture itself obtained in the method of the present invention for preparing sodium formyl acetone is supplied without isolating sodium formyl acetone from the reaction mixture, to a reaction vessel simultaneously with sulfuric acid so as to neutralize and acetalize sodium formyl acetone contained in said reaction mixture, the neutralizing and acetalizing reaction being carried out at a pH of 0 to 1.

Additional objects and advantages of the invention will be set forth in the description which follows, and in part will be obvious from the description, or may be learned by practice of the invention. The objects and advantages of the invention may be realized and obtained by means of combinations particularly pointed out in the appended claims.

DETAILED DESCRIPTION OF THE PREFERRED EMBODIMENTS

The method of the present invention for preparing sodium formyl acetone utilizes a reaction to form sodium formyl acetone and methanol as a by-product. As seen from reaction formula (1) given below, the rate of reaction to form sodium formyl acetone is retarded with increase in the initial methanol concentration of the reaction system. Also, since the reaction is carried out under a strong alkali, acetone is dimerized into diacetone alcohol as known to the art, as denoted by reaction formula (2). When the reaction further proceeds, methyl ether of diacetone alcohol is formed, as denoted by reaction formula (3).

$$CH_3COCH_3 + HCOOCH_3 + NaOMe \rightarrow CH_3COCH=CHONa + 2MeOH \quad (1)$$

$$2CH_3COCH_3 \rightarrow CH_3COCH_2-C(OH)(CH_3)CH_3 \quad (2)$$

$$CH_3COCH_2-C(OH)(CH_3)CH_3 + MeOH \rightarrow CH_3COCH_2-C(OCH_3)(CH_3)CH_3 + H_2O \quad (3)$$

It has been clarified that, if the rate of main reaction (1) is lowered, the side reactions (2) and (3) are relatively promoted so as to increase the formation of the by-products, i.e., diacetone alcohol and methyl ether of diacetone alcohol. In other words, the yield of the desired product sodium formyl acetone is lowered. In addition, the product quality is degraded. In order to find conditions which permit effectively promoting the main reaction (1), the present inventors tried a liquid phase reaction in which the acetone concentration of the reaction system was restricted and sodium methoxide was used in the form of a methanol solution, arriving at the method of the present invention which permits manufacturing sodium formyl acetone of high purity with a high yield. Naturally, the by-product formation can be markedly suppressed in the method of the present invention.

In the method of the present invention for preparing sodium formyl acetone, sodium methoxide is used in the form of a methanol solution containing 10 to 40% of sodium methoxide. Preferably, the sodium methoxide concentration of the solution should be 20 to 30% for effectively carrying out a liquid phase reaction. The molar ratio of acetone to sodium methoxide should fall within a range of preferably between 0.9 and 1.2, more preferably between 0.95 and 1.1. If the molar ratio of acetone is larger than 1.2, the excess acetone causes side reactions (2) and (3). If the molar ratio of acetone is smaller than 0.9, however, sodium methoxide partly remains unreacted. In this case, the unreacted sodium methoxide decomposes the desired product of sodium formyl acetone, leading to a low product yield.

The molar ratio of methyl formate to sodium methoxide should fall within a range of preferably between 1 and 10, more preferably between 1 and 3. The side reactions (2) and (3) can be suppressed by promoting the rate of main reaction (1). In this sense, it is desirable to use a larger amount of methyl formate. However, methyl formate has a low boiling point, i.e., 32° C., making it troublesome to recover methyl formate from the methanol solution. Thus, it is desirable in terms of economy to diminish the excess amount of methyl formate. Under the circumstances, it is particularly desirable to set the molar ratio of methyl formate to sodium methoxide to fall within a range of between 1.5 and 2.5.

In the present invention, acetone and methyl formate are added to a methanol solution of sodium methoxide. Acetone and methyl formate can be added separately or in the form of a mixture to the methanol solution of sodium methoxide. It should be noted that, if the acetone concentration of the reaction system is high, side reactions tend to take place, as pointed out previously.

It is desirable to add acetone slowly such that the acetone concentration of the reaction system does not exceed 5%, more desirably, 3%. Where the molar ratio of the reactants is set to fall within the range specified above, the reaction should be carried out for at least 1 hour, preferably at least 2 hours. (The reaction time means the sum of the dropping time and the stirring time after completion of the dropping.) The upper limit of the reaction time need not be restricted, though the reaction time does not exceed 10 hours in general in view of productivity in the industrial production of sodium formyl acetone.

For promoting the main reaction (1), the methyl formate concentration of the reaction system should desirably be high. However, the reaction system is strongly alkaline and, thus, decomposition of methyl formate also takes place. It follows that it is desirable to supply methyl formate simultaneously with acetone into the methanol solution of sodium methoxide such that the molar ratio of the reactants falls within the range specified above. For example, it is desirable to supply methyl formate in a molar amount two times as much as sodium methoxide and acetone equal in a molar amount to sodium methoxide simultaneously into the methanol solution containing sodium methoxide over 3 hours. The molar ratio of methyl formate to acetone should desirably fall within a range of between 1.5 and 3.0.

Either a batch type reaction or a continuous type reaction can be employed in the present invention. In the case of the batch type reaction, the reaction is carried out among the reactants mixed at the molar ratio specified previously. In the case of the continuous type reaction, above-mentioned molar ratio of acetone and methyl formate are simultaneously supplied to the methanol solution containing an above-mentioned molar ratio of sodium methoxide so as to carry out the desired reaction. The residence time should be at least 3 hours. In each of the batch type reaction and the continuous type reaction, it is desirable to stir sufficiently the reaction system. Thus, it is desirable to choose a reactor and a stirring vane adapted for the sufficient stirring of the reaction system depending on the type of reaction employed.

The reaction temperature should be determined in view of the rates of the main reaction and side reactions. Of course, the reaction temperature should be determined to achieve the highest rate of the main reaction. Where the molar ratio of the reactants falls within the range specified previously, the reaction should be carried out preferably at 10° to 60° C., more preferably at 25° to 50° C., and most preferably at 35° to 45° C. The reaction pressure is not particularly restricted in the present invention. However, since the reactants have low boiling points, it is desirable to carry out the reaction under a pressure ranging between the atmospheric pressure and somewhat higher pressure (1 to 2 $kg/cm^2G$) in order to prevent evaporation of the reactants from the reaction system. Where the reaction is carried out under atmospheric pressure, it is desirable to provide a condenser to the reactor such that the evaporated materials are condensed with cold water so as to achieve a sufficient reflux of methyl formate.

The reaction product of sodium formyl acetone can be purified by known industrial methods. For example, the reaction mixture is subjected to a known crystallizing operation such as condensation cooling method and solution evaporation method so as to separate and obtain sodium formyl acetone of high purity with a high yield. Sodium formyl acetone obtained by the method of the present invention, which can be used for the production of various chemical materials, is particularly useful in the production of medicines.

The present invention also provides a method of preparing 4,4-dimethoxy-2-butanone. Naturally, the reaction mixture obtained in the method of preparing sodium formyl acetone described above contains both sodium formyl acetone and methanol. In the present invention, for example, the reaction mixture noted above is supplied at a predetermined rate into a reaction vessel provided with a stirrer so as to carry out an acetalizing reaction between sodium formyl acetone and methanol. Sulfuric acid is also simulataneously supplied together with the reaction mixture into the reaction vessel so as to control the pH of the reaction liquid in the reaction vessel at 0 to 1. A concentrated sulfuric acid is preferably used as sulfuric acid and the concentrated sulfuric acid concentration falls within a range of preferably between 95% and 100%, more preferably between 98% and 100%.

The sodium formyl acetone concentration of the reaction mixture (methanol solution) is not particularly restricted in the present invention. It should be noted, however, that methanol is required for the acetalizing reaction. Also, if the sodium formyl acetone concentration of the reaction mixture is unduly high, the reaction mixture is in the form of a slurry, leading to a somewhat poor operability. Under the circumstances it is desirable to set the sodium formyl acetone concentration to fall within a range of preferably between 5 and 30% by weight. In practice, the reaction mixture obtained in the method of preparing sodium formyl acetone according to the present invention contains 18 to 25% by weight of sodium formyl acetone and the balance of substantially methanol. In this case, the reaction mixture slightly assumes a slurry form. It follows that it is desirable to add methanol to the reaction mixture or condense the reaction mixture appropriately so as to set the sodium formyl acetone concentration to fall within a preferred range of between 15 and 20% within which a slurry is not deposited.

Either a batch type reaction or a continuous type reaction can be employed in the method of the present invention for manufacturing 4,4-dimethoxy-2-butanone. In the case of the batch type reaction, methanol or a mixture of methanol and a small amount of sulfuric acid added to control the pH at 0 to 1 is charged in a reaction vessel provided with a stirrer such that the stirring vane is immersed in the charged methanol or mixture. Then, the reaction mixture, i.e., methanol solution of sodium formyl acetone, and a concentrated sulfuric acid are simultaneously supplied into the reaction vessel. As described previously, sulfuric acid is added in this step to control the pH of the reaction system at 0 to 1. After predetermined amounts of the reaction mixture and concentrated sulfuric acid are supplied to the reaction vessel, the reaction system should be kept stirred for preferably at least 1 hour, more preferably for 2 to 5 hours.

In the case of the continuous type reaction, the reaction is started as in the batch type reaction. In this case, the reactants are continuously fed to the reaction vessel and the reaction mixture is continuously discharged from the reaction vessel with the residence time set at 3 to 5 hours. Alternatively, it is desirable to control the reaction in a pH control vessel under a residence time of about 5 minutes to about 1 hour. In this case, the reaction mixture, i.e., a methanol solution of sodium formyl acetone, and sulfuric acid are simultaneously fed continuously into the pH control vessel, and the reaction system discharged from the pH control vessel by a suitable method, e.g., overflowing, is stirred and aged within a stirring vessel (reaction vessel). Of course, the reaction system is continuously discharged from the stirring vessel with the residence time within the stirring vessel set at 3 to 5 hours.

The simultaneous feeding of the methanol solution of sodium formyl acetone and concentrated sulfuric acid as employed in the present invention produces a prominent effect. According to the studies of the present inventors, in the method of neutralizing and acetalizing sodium formyl acetone, sulfuric acid is fed to a methanol solution of sodium formyl acetone. Alternatively, a methanol solution of sodium formyl acetone is supplied to a methanol solution of sulfuric acid. However, these techniques give rise to serious defects. In the technique of feeding sulfuric acid into a methanol solution of sodium formyl acetone, the pH of the reaction system is on the alkali side in the initial and middle stages of the reaction. Therefore, it is unavoidable to carry out the reaction on the alkali side in spite of the pH control in the initial stage. However, the reaction should be carried out under a strong acidic condition, i.e., under pH of at most 1, even in the initial stage of the reaction in order to obtain 4,4-dimethoxy-2-butanone with a satisfactorily high yield.

In the technique of supplying a methanol solution of sodium formyl acetone into a methanol solution of sulfuric acid, the pH of the reaction system is very low owing to the presence of the large amount of sulfuric acid in the initial stage of the reaction. In this technique, the pH of the reaction system rises gradualy as feeding is continued and is kept at a value falling within a range of at most 1 throughout the reaction stage, making it possible to improve the product yield to some extent. However, the present inventors have found that the particular technique necessitates sulfuric acid in an amount larger than the stoichiometric amount required for the neutralization and acetalization.

To be more specific, the neutralizing and acetalizing reaction in the present invention is carried out as follows:

The reaction formula given above indicates that, in the acetalizing reaction, the molar amount of sulfuric acid is stoichiometrically half the molar amount of sodium formyl acetone, which is markedly smaller than the amount of sulfuric acid required for maintaining the pH value at 0 to 1 and for the neutralization.

An unexpected phenomenon has been found, however, that, where a methanol solution of sodium formyl acetone is supplied into a methanol solution of sulfuric acid, sulfuric acid is not effectively utilized. It has been found that sulfuric acid in substantially the same molar amount as sodium formyl acetone is required in this case, as indicated below:

As apparent from the reaction formula given above, an equivalent of alkali is required for neutralizing the unreacted sodium hydrogensulfate after the reaction to form 4,4-dimethoxy-2-butanone. Clearly, it is advantageous to supply sulfuric acid to a reaction vessel together with a methanol solution of sodium formyl acetone as in the present invention.

It is desirable to carry out the neutralizing and acetalizing reaction at 0° to 70° C. In other words, it is desirable to mix the methanol solution of sodium formyl acetone and sulfuric acid at the temperature range noted above. Preferably, the reaction should be carried out at 20° to 50° C. If the reaction temperature is unduly low, it is difficult to achieve a sufficiently high reaction rate. On the other hand, an unduly high reaction temperature causes sodium formyl acetone or formyl acetone resulting from neutralization of sodium formyl acetone to be decomposed and deteriorated, leading to a low yield of 4,4-dimethoxy-2-butanone. After the reaction, the reaction mixture is neutralized with a suitable alkaline aqueous solution such as an aqueous solution of caustic soda, ammonia water, or an aqueous solution of caustic potash. Finally, the neutralized reaction mixture is refined by known unit operations such as concentration and distillation so as to obtain 4,4-dimethoxy-2-butanone of high purity.

Described in the following are Examples of the present invention.

EXAMPLE 1

579 g of 28% methanol solution of sodium methoxide (containing 3.0 mols of sodium methoxide) was charged in a four-neck flask having an inner volume of 2 liters and provided with a thermometer, a dropping funnel, a Dimroth condenser, a stirrer and an exhaust pipe connected to a draft. The solution was heated to 40° C., followed by dropping a liquid mixture consisting of 540 g (9.0 mols) of methyl formate and 191 g (3.3 mols) of acetone into the heated solution over a period of 3 hours. During the reaction, the reaction system was maintained at 40° C. and kept sufficiently stirred.

The stirring was continued for 1 hour after completion of the dropping. Then, the reaction mixture was subjected to a quantitative analysis with a liquid chromatography, finding that formed was 302 g (2.8 mols) of sodium formyl acetone (yield of 93.3% based on sodium methoxide). Also formed was about 8 g (0.06 mol) of a by-product methyl ether of diacetone alcohol.

EXAMPLE 2

A reaction to form sodium formyl acetone was carried out as in Example 1, except that the amount of acetone used was 174 g (3.0 mols). Formed was 292 g (2.7 mols) of sodium formyl acetone (yield of 90% based on sodium methoxide). Also formed was about 5 g (0.04 mol) of a by-product methyl ether of diacetone alcohol.

CONTROL 1

A reaction to form sodium formyl acetone was carried out by the method described in U.S. Pat. No. 2,760,985 referred to previously in the related art portion. Specifically, 180 g (3.0 mols) of methyl formate was charged in a flour-neck flask similar to that used in Example 1. Then, 162 g (3.0 mols) of a powdery sodium methoxide wa gradually added under cooling to the methyl formate charged in advance in the flask. The resultant system was heated for reflux for 15 minutes, followed by dropping 192 g (3.3 mols) of acetone into the system over a period of 15 minutes. The resultant reaction system was heated for reflux for 1 hour while stirring the system after completion of the dropping. Then, a quantitative analysis was performed as in Example 1, finding that formed was about 60 g (0.55 mol) of sodium formyl acetone (yield of 18.3% based on sodium methoxide). Also, the reaction mixture was found to be a slurry having a very high viscosity.

CONTROL 2

A reaction to form sodium formyl acetone was carried out as in Example 1, except that a liquid mixture consisting of 540 g (9.0 mols) of methyl formate and 191 (3.3 mols) of acetone was dropped into a methanol solution of sodium methoxide over a period of 30 minutes. Formed was 185 g (1.7 mols) of sodium formyl acetone (yield of 56.6% based on sodium methoxide). Also formed was about 55 g (0.51 mol) of a by-product methyl ether of diacetone alcohol.

EXAMPLES 3-9

579 g of 28% methanol solution of sodium methoxide (containing 3.0 mols of sodium methoxide) was charged in a four-neck flask as used in Example 1. The solution was maintained at 25° C., 40° C. or 50° C., and a liquid mixture consisting of 191 g (3.3 mols) of acetone and varied amounts of methyl formate shown in Table 1 was dropped into the methanol solution of sodium methoxide over a period of 3 to 10 hours so as to carry out a reaction to form sodium formyl acetone. The reaction was carried out under a pressure of 1 atm. (atmospheric pressure) or 2 atm. and a temperature of 25° C., 40° or 50° C. During the reaction, the reaction system was kept stirred sufficiently. After the reaction, the reaction mixture was subjected to a quantitative analysis of sodium formyl acetone with a liquid chromatography. Table 1 also the yield of sodium formyl acetone based on sodium methoxide and the formed amount of by-product methyl ether of diacetone alcohol.

TABLE 1

| Example or Control | Raw Material Molar Ratio | | | Dropping Time of MF + AC Liquid Mixture (hrs.) | Concentration of AC in the Reaction Liq. | | Reaction Temperature (°C.) | Reaction Pressure (atm.) | Fa.Na Yield (%) | DAM Formation (mol) |
|---|---|---|---|---|---|---|---|---|---|---|
| | SM | MF | AC | | average | MAx. | | | | |
| Example | | | | | | | | | | |
| 1 | 1 | 3 | 1.1 | 3 | 2.3 | 2.8 | 40 | 1 | 93.3 | 0.06 |
| 2 | 1 | 3 | 1.0 | 3 | 2.2 | 2.6 | 40 | 1 | 90.0 | 0.04 |
| 3 | 1 | 1.5 | 1.1 | 3 | 2.8 | 3.0 | 40 | 1 | 82.2 | 0.22 |
| 4 | 1 | 2 | 1.1 | 3 | 2.6 | 2.9 | 40 | 1 | 85.7 | 0.13 |
| 5 | 1 | 10 | 1.1 | 3 | 2.0 | 2.4 | 40 | 1 | 94.1 | 0.04 |
| 6 | 1 | 3 | 1.1 | 5 | 1.8 | 2.1 | 40 | 1 | 93.6 | 0.03 |
| 7 | 1 | 3 | 1.1 | 10 | 1.3 | 1.5 | 40 | 1 | 92.7 | 0.03 |
| 8 | 1 | 3 | 1.1 | 3 | 3.3 | 4.0 | 25 | 1 | 79.0 | 0.18 |
| 9 | 1 | 3 | 1.1 | 3 | 1.8 | 2.1 | 50 | 2 | 89.5 | 0.08 |

TABLE 1-continued

| Example or Control | Raw Material Molar Ratio | | | Dropping Time of MF + AC Liquid Mixture (hrs.) | Concentration of AC in the Reaction Liq. | | Reaction Temperature (°C.) | Reaction Pressure (atm.) | Fa.Na Yield (%) | DAM Formation (mol) |
| --- | --- | --- | --- | --- | --- | --- | --- | --- | --- | --- |
| | SM | MF | AC | | average | MAx. | | | | |
| Control | | | | | | | | | | |
| 1 | 1 | 1 | 1.1 | 15 (minutes) | — | — | 40 | 1 | 18.3 | — |
| 2 | 1 | 3 | 1.1 | 30 (minutes) | 7 | 9 | 40 | 1 | 56.6 | 0.51 |

Note:
SM: sodium metoxide 28% methanol solution charging of 579 g (3.0 mols)
MF: methyl formate
AC: acetone
FA.Na: sodium formyl acetone
DAM: diacetone alcohol methyl ether

EXAMPLE 10

A reaction to form sodium formyl acetone was carried out first. Specifically, 579 g of 28% methanol solution of sodium methoxide (containing 3.0 mols of sodium methoxide) was charged in a four-neck flask as used in Example 1. The solution was heated to 40° C., followed by dropping a liquid mixture consisting of 540 g (9.0 mols) of methyl formate and 191 g (3.3 mols) of acetone into the heated solution over a period of 3 hours. After completion of the dropping, the reaction system was kept stirred for 1 hour at 40° C. The reaction mixture was subjected to a quantitative analysis with a liquid chromatography, finding that formed was 298 g (2.76 mols) of sodium formyl acetone (yield of 92% based on sodium methoxide).

On the other hand, 600 ml of methanol was charged in a four-neck flask having an inner volume of 3 liters and provided with a pH meter, a thermometer, a dropping funnel, a stirrer and an exhaust pipe connected to a draft. The charged methanol was maintained at 30° C., and a small amount (about 10 g) of concentrated sulfuric acid (100% concentrated sulfuric acid) was added to the charged methanol to control the pH at 0.2. Then, the methanol solution of sodium formyl acetone, i.e., the reaction mixture obtained in the reaction to form sodium formyl acetone described above, was dropped into the flask. A concentrated sulfuric acid was also dropped together with the reaction mixture into the flask so as to control the p of the reaction system to fall within a range of between 0 and 1. The reaction mixture and concentrated sulfuric acid were dropped over a period of about 1 hour. The dropped amount of the concentrated sulfuric acid was 152 g (1.55 mols).

After completion of the dropping, the reaction system was kept stirred for 4 hours at 30° C., followed by neutralizing the reaction system with a 20% aqueous solution of caustic soda to set the pH at 7. The neutralized reaction mixture was analyzed with a gas chromatography, finding that formed was 317 g (2.40 mols) of 4,4-dimethoxy-2-butanone (yield of 87% based on sodium formyl acetone and 80% based on sodium methoxide).

CONTROL 3

4,4-dimethoxy-2-butanone was prepared by the method based on the method of U.S. Pat. No. 2,760,985 referred to previously in the related art portion. Specifically, 162 g (3.0 mols) of a powdery sodium methoxide was charged in a flask as used in Example 1, followed by charging 1.4 liters of methylene chloride in the flask. The resultant system was cooled to 5° C., followed by adding 180 g (3.0 mols) of methyl formate to the system. The mixture was heated for reflux for 15 minutes and, then, cooled to room temperature. Then, 191 g (3.3 mols) of acetone was dropped into the mixture over a period of 15 minutes. After completion of the dropping, the reaction system was heated for reflux for 1 hour. Sodium formyl acetone formed by the reaction was recovered from the reaction mixture by filtration, followed by drying the product sodium formyl acetone.

In the next step, 1.3 liters of a 5N methanol solution of hydrochloric acid was charged in a four-neck flask having an inner volume of 5 liters and provided with a pH meter, a thermometer, a dropping funnel, a stirrer and an exhaust pipe connected to a draft. Then, a solution prepared by dissolving the solid sodium formyl acetone obtained in the previous process in 2 liters of methanol was dropped at 20° C. into the methanol solution of hydrochloric acid over a period of 30 minutes. After completion of the dropping, the reaction system was kept stirred for 4 hours, followed by neutralizing the reaction system with a 20% aqueous solution of caustic soda to set the pH at 7.

The reaction mixture was analyzed with a gas chromatography, finding that formed was 195 g (1.48 mols) of 4,4-dimethoxy-2-butanone (yield of 49% based on sodium methoxide).

CONTROL 4

Sodium formyl acetone was prepared as in Example 10. On the other hand, 1.2 liters of methanol and 170 g (1.7 mols) of concentrated sulfuric acid (100% concentrated sulfuric acid) were charged in a four-neck flask having an inner volume of 3 liters and provided with a pH meter, a thermometer, a dropping funnel, a stirrer, and an exhaust pipe connected to a draft. Then, the methanol solution of sodium formyl acetone, i.e., the reaction mixture obtained in the reaction to form sodium formyl acetone, was dropped into the flask over a period of 1 hour while keeping the liquid temperature at 30° C. After completion of the dropping, the reaction system was kept stirred for 4 hours at 30° C., followed by neutralizing the reaction system with a 20% aqueous solution of caustic soda to set the pH at 7. The reaction mixture was analyzed with a gas chromatography, finding that formed was 146 g (1.1 mols) of 4,4-dimethoxy-2-butanone (yield of 37% based on sodium methoxide).

CONTROL 5

The process to form 4,4-dimethoxy-2-butanone was carried out as in Control 4, except that 100% concentrated sulfuric acid was charged in an amount of 294 g (3.0 mols). Formed was 220 g (1.67 mols) of 4,4-dimethoxy-2-butanone (yield of 56% based on sodium methoxide).

EXAMPLES 11 to 17

The process to form 4,4-dimethoxy-2-butanone was carried out as in Example 10, except that the reacting conditions such as simultaneous feeding time of sodium formyl acetone and 100% concentrated sulfuric acid, the reaction time after completion of the feeding, and the reaction temperature were set as shown in Table 2. The yield of the product 4,4-dimethoxy-2-butanone is also shown in Table 2.

TABLE 2

| Example or Control | Raw Material Molar Ratio | | | Dropping Time of MF + AC Liquid Mixture (hrs.) | Concentration of AC in the Reaction Liq. (%) | | Reaction Temp. <1st step> (°C.) | Reaction Pressure (atm.) | Fa.Na Yield (%) | Feeding Time of FA.Na + $H_2SO_4$ (hrs.) | Reaction Time after Completion of Feeding (hrs.) | Reaction Temp. <2nd step> (°C.) | DMB Yield | |
|---|---|---|---|---|---|---|---|---|---|---|---|---|---|---|
| | SM | MF | AC | | average | MAx. | | | | | | | based on SM (%) | based on FA.Na (%) |
| Example 10 | 1 | 3 | 1.1 | 3 | 2.2 to 2.4 | 3.0 | 40 | 1 | 92.0 | 1 | 4 | 30 | 80 | 87 |
| Control | | | | | | | | | | | | | | |
| 3 | 1 | 1 | 1.1 | 15 (minutes) | 5 | 7 | 25 | 1 | 61.5 | (HCl) 0.5 | 4 | 20 | 40 | 80 |
| 4 | 1 | 3 | 1.1 | 3 | 2.2 to 2.4 | 3.0 | 40 | 1 | 92.0 | 1 | 4 | 30 | 37 | 40 |
| 5 | 1 | 3 | 1.1 | 3 | " | " | 40 | 1 | 92.0 | 1 | 4 | 30 | 56 | 61 |
| Example | | | | | | | | | | | | | | |
| 11 | 1 | 3 | 1.1 | 3 | 2.2 to 2.4 | 3.0 | 40 | 1 | 92.0 | 2 | 4 | 30 | 81 | 88 |
| 12 | 1 | 3 | 1.1 | 3 | " | " | 40 | 1 | 92.0 | 1 | 8 | 30 | 79 | 86 |
| 13 | 1 | 3 | 1.1 | 3 | " | " | 40 | 1 | 92.0 | 1 | 2 | 30 | 74 | 80 |
| 14 | 1 | 3 | 1.1 | 3 | " | " | 40 | 1 | 92.0 | 1 | 1 | 30 | 66 | 72 |
| 15 | 1 | 3 | 1.1 | 3 | " | " | 40 | 1 | 92.0 | 1 | 4 | 20 | 73 | 79 |
| 16 | 1 | 3 | 1.1 | 3 | 2.2 to 2.4 | 3.0 | 40 | 1 | 92.0 | 1 | 4 | 40 | 78 | 85 |
| 17 | 1 | 3 | 1.1 | 3 | " | " | 40 | 1 | 92.0 | 1 | 4 | 60 | 70 | 76 |

Note:
SM: sodium metoxide 28% methanol solution charging of 579 g (3.0 mols)
MF: methyl formate
AC: acetone
FA.Na: sodium formyl acetone
DMB: 4,4-dimethoxy-2-butanone In the method of the present invention for manufacturing sodium formyl acetone, the acetone concentration in the reaction system is restricted, and sodium methoxide is used in the form of a methanol solution. The particular method of the present invention using the liquid phase reaction makes it possible to obtain sodium formyl acetone with a high yield, markedly suppressing the by-product formation.

The present invention also provides a method of manufacturing 4,4-dimethoxy-2-butanone. In this method, a methanol solution of sodium formyl acetone, which is obtained as a reaction mixture in the reaction to form sodium formyl acetone, is directly charged in a reaction vessel together with sulfuric acid for the neutralizing and acetalizing reaction. The particular method using neutralizing and acetalizing reaction by sulfuric acid in methanol solution permits commercially manufacturing 4,4-dimethoxy-2-butanone with a high yield without employing the step of separating and recovering methanol.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of preparing sodium formyl acetone using acetone, methyl formate and sodium methoxide as raw materials, wherein a mixture of acetone and methyl formate is supplied into a methanol solution of sodium methoixde, or an acetone and a methyl formate are separately supplied simultaneously into a methanol solution of sodium methoxide, and the raw materials are mixed to form a reaction mixture, the mixing being conducted over a predetermined period of time such that acetone concentration in the reaction mixture does not exceed 5%, so as to react acetone with methyl formate and sodium methoxide.

2. The method of claim 1 wherein the reaction mixture is further supplied to a reaction vessel simultaneously with sulfuric acid so as to neutralize and acetalize sodium formyl acetone contained in said reaction mixture, neutralizing and acetalizing sodium formyl acetone being carried out at a pH of 0 to 1.

3. The method according to claim 1, wherein the sodium methoxide concentration in the methanol solution falls within a range of between 10 and 40%.

4. The method according to claim 1, wherein the molar ratio of acetone to sodium methoxide falls within a range of between 0.89 and 1.2.

5. The method according to claim 1, wherein the molar ratio of methyl formate to sodium methoxide falls within a range of between 1 and 10.

6. The method according to claim 1, wherein the reaction time is at least 1 hour.

7. The method according to claim 1, wherein methyl formate in a molar amount 1 to 3 times as much as sodium methoxide and acetone in molar amount 0.95 to 1.1 times as much as sodium methoxide are simultaneously supplied to the methanol solution of sodium methoxide over a period of at least 2 to 10 hours.

8. The method according to claim 1, wherein the reaction temperature falls within a range of between 10° C. and 60° C.

9. The method according to claim 1, wherein the reaction pressure falls within a range of between the atmospheric pressure and 2 kg/cm$^2$G.

10. The method according to claim 1, wherein the reaction is carried out in a batch system.

11. The method according to claim 1, wherein the reaction is carried out in a continuous system.

12. The method according to claim 2, wherein the sodium formyl acetone concentration in said reaction mixture falls within a range of between 5 and 30% by weight.

13. The method according to claim 2, wherein the reaction temperature falls within a range of between 0° C. and 70° C.

14. The method according to claim 2, wherein the reaction is carried out in a batch system.

15. The method according to claim 2, wherein the reaction is carried out in a continuous system.

* * * * *

UNITED STATES PATENT AND TRADEMARK OFFICE
CERTIFICATE OF CORRECTION

PATENT NO. : 5,276,200
DATED : January 4, 1994
INVENTOR(S) : Keigo Nishihira, et. al.

It is certified that error appears in the above-indentified patent and that said Letters Patent is hereby corrected as shown below:

Title page, item [73], Assignee: delete "Yamagushi" and insert therefor--Yamaguchi--.
Column 8, line 11, delete "wa" and insert therefor--was--.
Column 8, line 27, after the numeral "191", insert --g--.
Table 1, col. 20, line 2, delete "Fa.Na" and insert therefor --Fa˙Na--.
      col. 21, line 2, delete "Fa.Na" and insert therefor --Fa˙Na--.
Table 2, col. 27, line 2, delete "Fa.Na" and insert therefor --Fa˙Na--.
          28, line 4, delete "Fa.Na" and insert therefor --Fa˙Na--
             line 5, delete "Fa.Na" and insert therefor --Fa˙Na--.
          30, line 13, delete "Fa.Na and insert therefor --Fa˙Na--.
Column 9, line 44, delete "p" and insert therefor --pH--.
Column 12, line 54, delete "0.89" and insert therefor-- 0.09--.

Signed and Sealed this

Twenty-sixth Day of September, 1995

Attest:

BRUCE LEHMAN

Attesting Officer        Commissioner of Patents and Trademarks